(12) United States Patent
Dobbing

(10) Patent No.: US 10,843,014 B2
(45) Date of Patent: Nov. 24, 2020

(54) RESPIRATOR MASK MANAGEMENT SYSTEM

(71) Applicant: Christopher Dobbing, Beijing (CN)

(72) Inventor: Christopher Dobbing, Beijing (CN)

( * ) Notice: Subject to any disclaimer, the term of this patent is extended or adjusted under 35 U.S.C. 154(b) by 421 days.

(21) Appl. No.: 15/781,844

(22) PCT Filed: Dec. 6, 2016

(86) PCT No.: PCT/IB2016/001888
§ 371 (c)(1),
(2) Date: Jun. 6, 2018

(87) PCT Pub. No.: WO2017/098329
PCT Pub. Date: Jun. 15, 2017

(65) Prior Publication Data
US 2018/0369616 A1 Dec. 27, 2018

(30) Foreign Application Priority Data

Dec. 7, 2015 (GB) .................................. 1521531.2

(51) Int. Cl.
*A62B 9/00* (2006.01)
*A62B 7/10* (2006.01)
(Continued)

(52) U.S. Cl.
CPC ................ *A62B 9/006* (2013.01); *A62B 7/10* (2013.01); *A62B 18/08* (2013.01); *A62B 18/088* (2013.01);
(Continued)

(58) Field of Classification Search
CPC ......... A62B 7/10; A62B 18/088; A62B 18/10; A62B 23/00; A62B 23/02; A62B 23/025; A62B 23/04; A62B 23/06
See application file for complete search history.

(56) References Cited

U.S. PATENT DOCUMENTS

| | | | |
|---|---|---|---|
| 5,950,621 A * | 9/1999 | Klockseth | A62B 9/006 128/204.26 |
| 2002/0020410 A1* | 2/2002 | Rydin | A61M 16/024 128/200.24 |

(Continued)

FOREIGN PATENT DOCUMENTS

| CN | 1464793 A | 12/2003 |
|---|---|---|
| CN | 203816108 U | 9/2014 |

(Continued)

OTHER PUBLICATIONS

Zhen Zhang, International Search Report for PCT/IB2016001888, dated Apr. 28, 2017, State Intellectual Property Office of the P.R. China.

*Primary Examiner* — Samchuan C Yao
*Assistant Examiner* — Nathan M Le

(57) ABSTRACT

Disclosed is a respirator mask management system. The respirator mask management system comprises a database storage, a data processing unit operatively coupled to the database storage, a user mobile device communicatively coupled with the data processing unit over a communication network, and a respirator mask including a filter configured to prevent inhalation of pollutants by a user, an exhalation valve, a sensor configured to determine a state of the exhalation valve, and a microprocessor operatively coupled with the sensor and having a wireless connectivity to the user mobile device for transmitting the sensed states of the exhalation valve to a respirator mask manager of the user mobile device.

14 Claims, 4 Drawing Sheets

(51) Int. Cl.
  *A62B 23/02* (2006.01)
  *A62B 27/00* (2006.01)
  *A62B 18/10* (2006.01)
  *G16H 40/67* (2018.01)
  *A61M 16/06* (2006.01)
  *H04W 88/02* (2009.01)
  *H04W 88/08* (2009.01)
  *A62B 18/08* (2006.01)
  *A62B 18/02* (2006.01)

(52) U.S. Cl.
  CPC ............ *A62B 18/10* (2013.01); *A62B 23/025* (2013.01); *A62B 27/00* (2013.01); *G16H 40/67* (2018.01); *A61M 16/06* (2013.01); *A61M 2205/273* (2013.01); *A61M 2205/7581* (2013.01); *A62B 18/025* (2013.01); *H04W 88/02* (2013.01); *H04W 88/08* (2013.01)

(56) References Cited

U.S. PATENT DOCUMENTS

| | | | |
|---|---|---|---|
| 2004/0168689 A1* | 9/2004 | Kuriyama | A62B 18/10 128/206.15 |
| 2010/0078017 A1 | 4/2010 | Andrieux et al. | |
| 2010/0078024 A1 | 4/2010 | Andrieux et al. | |
| 2010/0313892 A1 | 12/2010 | Shigematsu et al. | |
| 2015/0020800 A1* | 1/2015 | Tobias | A62B 18/088 128/202.22 |
| 2016/0121144 A1* | 5/2016 | Hyde | A62B 23/025 128/206.11 |
| 2019/0064750 A1* | 2/2019 | Awiszus | A61F 11/14 |

FOREIGN PATENT DOCUMENTS

| | | |
|---|---|---|
| EP | 2486959 | 12/2015 |
| JP | 2011078605 A | 4/2011 |

* cited by examiner

RESPIRATOR MASK MANAGEMENT SYSTEM

TECHNICAL FIELD

The present disclosure relates generally to a respirator mask; and more specifically, to a respirator mask management system for managing various aspects associated with a use of a respirator mask.

BACKGROUND

Air pollution has become a globally recognized challenge, and in 2014 the World Health Organization (WHO) has classified air pollution as a Group 1 carcinogenic to humans. Further, figures show that over 8 million people per year die from air pollution related illnesses. The most common solution to fight this problem is to use a respirator mask. Typically, the respirator mask is designed to protect a user or a wearer from inhaling harmful particulates, such as dusts, fumes, vapours, or gases. Moreover, in places and profession where people are subjected to such harmful particulates the use of respirator mask becomes a compulsion.

Generally, such respirator masks include a filter made of, for example, cloth, wet sponge or any other suitable material capable of preventing inhalation of harmful particulates. Further, the respirator masks may be divided into two categories in terms of usages-time thereof, i.e. a disposable type (use-and-throw) and a non-disposable (long term use). The non-disposable type respirator masks are generally associated with a pre-determined standard usages-time (i.e. how long such respirator masks can be suitably used without changing a filter thereof). However, there is no efficient way to identify when the filter of such respirator mask should be changed, as the user of the respirator mask may be subjected to different levels of air pollution on different days, and therefore the pre-determined standard usages-time may not be always applicable to such non-disposable respirator mask. In such instance, the use of such non-disposable respirator mask may cause (or pose) air pollution related illnesses to the user. Additionally, there are also other aspects (associated with the use of a respirator mask), such as time and duration of wearing such respirator mask, which may be taken into consideration for more efficiently using of such respirator mask.

Therefore, in light of the foregoing discussion, there exists a need to overcome the aforementioned drawbacks of conventional non-disposable respirator mask.

SUMMARY

The present disclosure seeks to provide a respirator mask management system.

The present disclosure also seeks to provide a method for respirator mask management.

The present disclosure also seeks to provide a method for managing a respirator mask.

In one aspect, an embodiment of the present disclosure provides a respirator mask management system, comprising:
  a database storage;
  a data processing unit operatively coupled to the database storage;
  a user mobile device communicatively coupled with the data processing unit over a communication network, the user mobile device including a respirator mask manager; and
  a respirator mask including a filter configured to prevent inhalation of pollutants by a user, an exhalation valve, a sensor configured to determine a state of the exhalation valve, and a microprocessor operatively coupled with the sensor and having a wireless connectivity to the user mobile device for transmitting sensed states of the exhalation valve to the respirator mask manager.

Optionally, the respirator mask manager is configured to receive from the microprocessor the sensed states of the exhalation valve, determine whether a number of state changes experienced by the exhalation valve over a time interval exceeds a pre-established threshold, and present a message to a display of the user mobile device indicating the filter is in need of replacement when the number of changed states experienced by the exhalation valve over the time interval exceeds the pre-established threshold.

Optionally, the respirator mask manager is further configured to present a button to the display of the user mobile device the actuation of which by the user presents an online order form for a replacement filter.

Optionally, the respirator mask manager is further configured to:
  cache, on the user mobile device, the sensed states of the exhalation valve transmitted by the microprocessor; and
  relay the sensed states to the database storage through the data processing unit.

More optionally, the respirator mask manager is further configured to:
  receive, from the data processing unit, accumulated data regarding previously stored sensed states of the exhalation valve; and
  present the accumulated data to the display of the user mobile device.

Optionally, the accumulated data regarding the previously stored sensed states of the exhalation valve include times of day during which the respirator mask was used; pollution levels at the time the respirator mask was used; and an amount of time, a number of breaths, or a number of state changes remaining before the filter will need replacement.

Optionally, the microprocessor is programmed to scan for one or more wireless access points to the communication network and when a scan discovers at least one wireless access point, to collect a wireless access point identifier.

More optionally, the respirator mask manager is configured to derive an approximate position of the respirator mask from the wireless access point identifier.

In another aspect, an embodiment of the present disclosure provides a method for respirator mask management, comprising:
  providing a database storage;
  providing a data processing unit operatively coupled to the database storage;
  providing a user mobile device communicatively coupled with the data processing unit over a communication network and including a respirator mask manager; and
  providing a respirator mask including a filter configured to prevent inhalation of pollutants by a user and an exhalation valve;
    with a sensor mounted on the exhalation valve, determining a state of the exhalation valve; and
    with a microprocessor housed in the respirator mask and operatively coupled with the sensor, transmitting the sensed states of the exhalation valve to the respirator mask manager.

In yet another aspect, an embodiment of the present disclosure provides a method for managing a respirator mask, comprising:
  with a sensor, measuring activation of an exhalation valve of the respirator mask;

waking up a microprocessor provided in a housing of the exhalation valve;

with the microprocessor, storing an exhalation valve data to a memory of the microprocessor in association with a unique time stamp, each of the exhalation valve activation being measured by the sensor;

with a communication module of the microprocessor, scanning for one or more wireless access points; and when the scanning for the one or more wireless access points discovers a user mobile device, transmitting the stored exhalation valve data to the user mobile device over a communication network.

Optionally, when the number of stored exhalation valve activations exceeds a pre-established threshold, illuminating a light-emitting diode of the microprocessor.

Optionally, when the scanning for the one or more wireless access points discover a wireless access point, transmitting the stored exhalation valve data to a data processing unit over the communication network without transmitting to the user mobile device.

Optionally, the method further comprises
upon expiration of a time interval measured from the last measured exhalation valve activation, waking up the microprocessor;
with the microprocessor, repeating the scanning and transmitting; and
with the microprocessor, checking the microprocessor, the sensor or both for errors.

Embodiments of the present disclosure substantially eliminate or at least partially address the aforementioned problems in the prior art, and provides an efficient respirator mask and a management system thereof.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION

Figure 1:
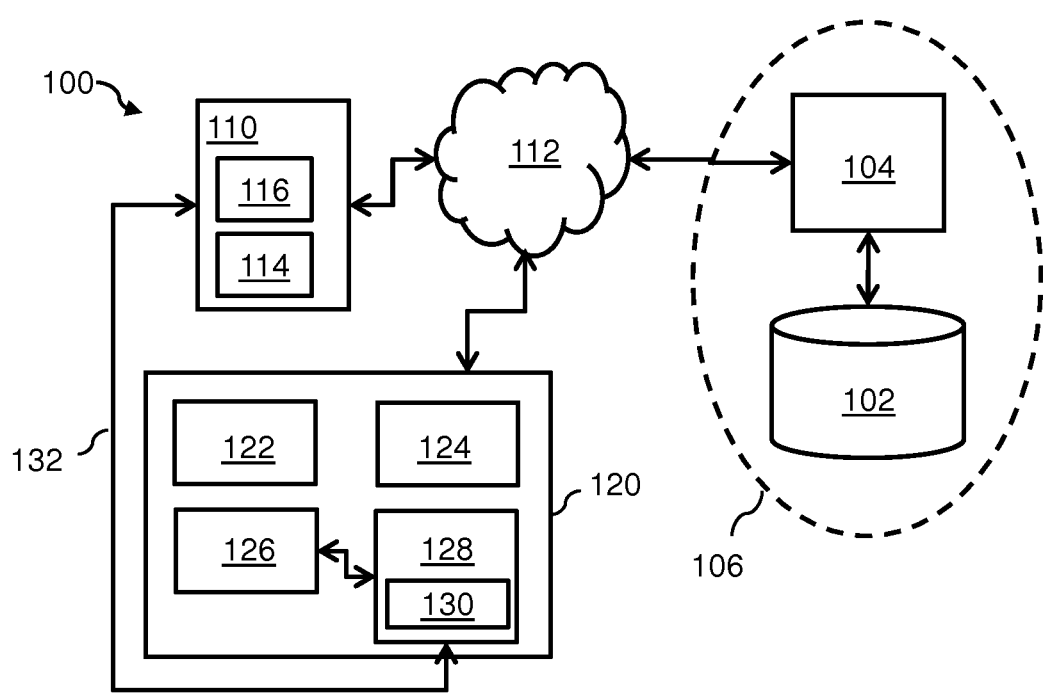
FIG. 1 is a block diagram of a respirator mask management system, in accordance with an embodiment of the present disclosure.

Referring to FIG. 1, illustrated is a schematic illustration of a respirator mask management system 100 (hereinafter may be referred to as the system 100), in accordance with an embodiment of the present disclosure. The system 100 includes a database storage 102 and a data processing unit 104 operatively coupled to the database storage 102. In other words, the system 100 may include a server 106 having the database storage 102 and the data processing unit 104. Otherwise, the system 100 may include separate computing devices, such as at least one database storage and separate at least one data processing unit (but operatively coupled to the such at least one database storage). Alternatively, the system 100 may include a plurality of servers.

The system 100 also includes a user mobile device 110 communicatively coupled to the data processing unit 104 over a communication network 112, which can be wired, wireless or a combination thereof. According to an embodiment, the communication network 112 includes, but is not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, and Worldwide Interoperability for Microwave Access (WiMAx) networks.

The user mobile device 110 includes a respirator mask manager 114, i.e. a software product (having a set of instructions) that can be executed by a processor of the user mobile device 110 for directing the user mobile device 110 to perform specific operations or functions, which will be explained in greater detail herein later.

The system 100 also comprises a respirator mask 120, which may be associated with a user for preventing himself or herself from air pollution related illnesses. The respirator mask 120 includes a filter 122 configured to prevent inhalation of pollutants by the user and an exhalation valve 124 for regulating flow of air through the filter 122. The filter 122 may be made of material, which may include but not limited to, cloth, foam material, fibres (plastic or metallic) or any combination thereof.

The respirator mask 120 also includes a sensor 126 configured to determine state of the exhalation valve 124 and a microprocessor 128 operatively coupled with the sensor 126. According to an embodiment, the microprocessor 128 includes a wireless communication interface 130 providing a wireless connectivity with the user mobile device 110. The wireless communication interface 130 enables the respirator mask 120 to transmit the sensed states of the exhalation valve 124 to the user mobile device 110, i.e. to the respirator mask manager 114. In one embodiment, the wireless communication interface 130 includes one of Wi-Fi and Bluetooth.

In operation, when the user inhales and exhales, the exhalation valve 124 closes and opens, respectively. In other words, when the user inhales and exhales, the exhalation valve 124 gets deactivated and activated, respectively. Specifically, the exhalation valve 124 is configured to open and let exhaled air move out of the respirator mask 120 freely without having to go through the filter 122, and close when the user is breathing in. The opening and closing of the exhalation valve 124 may be referred to as states of the exhalation valve 124. Therefore, the states of the exhalation valve 124 include opening and closing of the exhalation valve 124 during the time of exhalation and inhalation, respectively. Accordingly, count of the states of the exhalation valve 124 corresponds to a number of breaths taken by the user while wearing the respiratory mask 120.

The sensor 126 is operable to measure states (activation and deactivation) of the exhalation valve 124. Specifically, the sensor 126 determines whether the exhalation valve 124 is opened or closed. Further, based on this how many times the exhalation valve 124 has opened and closed is determined. In an embodiment, the sensor 126 is a magnet and a hall-sensor arrangement configured to determine whether the exhalation valve 124 is opened or closed. The sensor 126 may be arranged on a housing of the exhalation valve 124. The housing of the exhalation valve 124 also encompasses the microprocessor 128 and at least one battery (not shown). The microprocessor 128 and the sensor 126 are electrically powered by the battery.

According to an embodiment, the microprocessor 128 is generally configured to remain in a sleep mode by default using low amount of electrical power from the battery. However, the microprocessor 128 is configured to wakeup upon expiration of a pre-determined time interval. Alternatively, the microprocessor 128 may be configured to wakeup when the exhalation valve 124 gets activated, i.e. when the respiratory mask 120 is worn and the user starts breathing, which causes opening and closing of the exhalation valve 124. Further, microprocessor 128 is configured to store the exhalation valve 124 data (measured with the help of the sensor 126) in a memory of the microprocessor 128. Further, while storing the data in the memory, the microprocessor 128 is configured to assign a unique time stamp to such data. The time stamp enables in determining when and for how long the respiratory mask 120 was worn by the user.

In an embodiment, the stored data of the exhalation valve 124 is transmitted with the help of wireless communication interface 130 to the user mobile device 110. Specifically, the wireless communication interface 130 of the microprocessor 128 scans for wireless access points, such as the Wi-Fi or Bluetooth access points (or connectivity) for the user mobile device 106 for establishing the wireless connectivity therebetween and thereby transmitting the stored data of the exhalation valve 124 from the respiratory mask 120 to the user mobile device 110. In an embodiment, after transmitting the stored exhalation valve 124 data to the user mobile device 110, the microprocessor 128 goes back to the sleep mode.

The data of the exhalation valve 124 may be further communicated to the database storage 102 through the data processing unit 104 (operatively coupled to the database storage 102). The data processing unit 104 may be configured to process the exhalation valve 124 data (or the sensor 126 data) to determine the number of breaths, when and for how long the respiratory mask 120 was worn and the like. Alternatively, the user mobile device 110 and the microprocessor 128 may also enable in partially processing the data of the exhalation valve 124 to determine aspects associated with the use of a respirator mask 120. Thereafter, the processed data (determined number of breaths, when and for how long the respiratory mask 120 was worn and the like) may be sent to and stored in the data processing unit 104.

In another embodiment, the data of the exhalation valve 124 may be directly communicated to the database storage 102 (through the data processing unit 104) instead of being communicated by the user mobile device 110. Specifically, the microprocessor 128 is programmed to scan for one or more wireless access points to (or of) the communications network 112 and when a scan discovers at least one wireless access point, the microprocessor 128 is programmed to collect a wireless access point identifier. Further, the respirator mask manager 114 is configured to derive an approximate position of the respiratory mask 120 from the wireless access point identifier. In other words, the wireless communication interface 130 of the microprocessor 128 may scan for the wireless access points, associated with the communication network 112 for directly transmitting the data of the exhalation valve 124 to the database storage 102. Further, based on position of the wireless access point, a geographical location (or position) of the respiratory mask 120 may be identified. Otherwise, based on a geographical location of the user mobile device 110 (communicably coupled to the respiratory mask 120 and is in proximity of the user mobile device 110) the geographical location of the respiratory mask 120 may be identified. Alternatively, the respiratory mask 120 may be employed with a global positioning system (GPS) sensor (operatively coupled to the microprocessor 128) for identifying the geographical location of the respiratory mask 120. In such instance, the geographical location of the respiratory mask 120 may be identified even when the respiratory mask 120 is away from the user mobile device 110.

It is to be understood that the function of the system 100 explained herein above is associated with the respirator mask manager 114 of the user mobile device 110. The respirator mask manager 114 is an application running in the user mobile device 110 and may be installed from the server 106. Specifically, the respirator mask manager 114 is configured to receive from the microprocessor 128 the sensed states of the exhalation valve 124. Further, the respirator mask manager 114 determines whether a number of state changes experienced by the exhalation valve 124 over a time interval (for example, a week or a month) exceed a pre-established threshold. Furthermore, the respirator mask manager 114 presents a message to a display 132 of the user mobile device 110 indicating the filter 122 is in need of replacement when the number of changed states experienced by the exhalation valve 124 over a time interval exceeds the pre-established threshold.

In an example, the pre-established threshold may be 10000 state changes (or breaths). In such instance, if the state changes are more than 10000 times, then the respirator mask manager 114 presents the message on the display 132 of the user mobile device 110 indicating the filter 122 is in need of replacement. Further, when the number of stored exhalation valve 124 activations (i.e. the number of state changes) exceeds the pre-established threshold, the respirator mask manager 114 is configured to illuminate a light-emitting diode of the microprocessor 128 (i.e. the message is presented by illuminating a light-emitting diode of the microprocessor 128). In another embodiment, the message can be presented in the form of a sound to remind the user of the replacement of the filter 122. In yet another embodiment, the message can be presented in the form of a normal text message notification or an e-mail notification on the display 132 of the user mobile device 110.

In an embodiment, the respirator mask manager 114 is further configured to present a button to the display 132 of the user mobile device 110 the actuation of which by the user presents an online order form for a replacement filter. Further, the respirator mask manager 114 is configured to cache, on the user mobile device 110, the sensed states of the exhalation valve 124 transmitted by the microprocessor 128, and thereafter relay the sensed states to the database storage 102 through the data processing unit 104. In an embodiment, the respirator mask manager 114 is further configured to wake up the microprocessor 128 upon expiration of a time interval measured from the last measured exhalation valve activation; repeating the scanning and transmitting with the microprocessor 128; and checking the microprocessor 128, the sensor 126 or both for errors, with the help of microprocessor 128.

Moreover, the respirator mask manager 114 is configured to receive, from the data processing unit 104, accumulated data regarding previously stored sensed states of the exhalation valve 124; and present the accumulated data to the display 132 of the user mobile device 110. The accumulated data regarding the previously stored sensed states of the exhalation valve 124 include times of day during which the respirator mask 120 was used; pollution levels at the time the respirator mask 120 was used; and an amount of time, a number of breaths, or a number of state changes remaining before the filter 122 will need replacement. In an embodiment, the pollution levels are associated with the geographical location of the respirator mask 120 (i.e. the geographical location of the user wearing the respirator mask 120) and the data processing unit 104 receives the pollution levels from weather reports of the meteorological department of such the geographical location.

According to an embodiment, various elements of the respirator mask 120 may be implemented in a form of an electronic circuitry. For example, the elements, such as the sensor 126, the microprocessor 128 and the wireless communication interface 130 may be arranged on a printed circuit board. In an example, the sensor 126 may include a hall sensor, such as DRV5053 Analog Bipolar Hall Effect sensor from Texas Instruments®. Further, the wireless communication interface 130 may include Multiprotocol Bluetooth® low energy system on chip, for example, nRF51822 system on chip from Nordic Semiconductor®. In one embodiment, the electronic circuitry may also include other electronic components, such as a voltage regulator, an accelerometer, a pressure sensor, a temperature sensor, a balun, a battery charger, USB OTG, light emitting diodes (LEDs), and button. In an example, the voltage regulator may be a 3 volt (V) voltage regulator to maintain a constant voltage level. In an example, the accelerometer may be triple axis accelerometer, such as MMA8452Q from SparkFun Electronics®. The accelerometer may be operable to provide data regarding operating state of the respirator mask 120, i.e. presence of sensed (or measured) data associated with the accelerometer may be an indication used state of the respirator mask 120 and presence of sensed data may be an indication of unused state of the respirator mask 120. In an example, the pressure sensor may be an ultra-compact absolute piezoresistive pressure sensor, such as LPS331AP from STMicroelectronics®. In an example, the balun may be an impedance matched balun with band pass filter, such as 2450BM14E0003 from Nordic Semiconductor®. In an example, the LEDs may include red and green LEDs, such as may be 2 mA LEDs.

Figure 2:
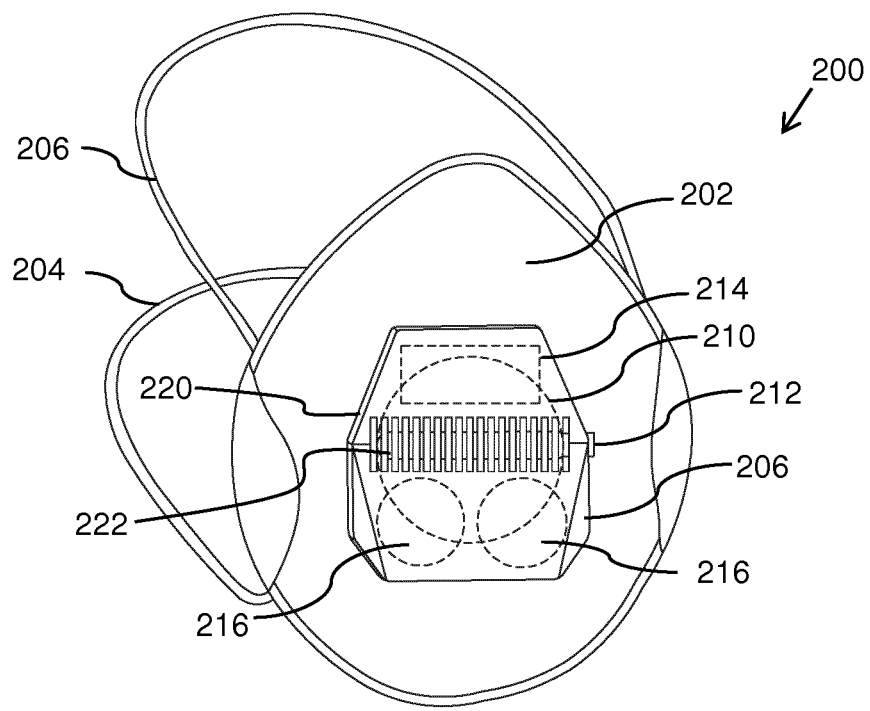
FIG. 2 is a schematic illustration of a respirator mask, in accordance with an embodiment of the present disclosure.

Referring to FIG. 2, illustrated is a schematic illustration of a respirator mask 200 (such as the respirator mask 120 of FIG. 1), in accordance with an embodiment of the present disclosure. As shown, the respirator mask 200 includes a cover member 202 and threads 204, 206 attached to the cover member 202. As shown, the cover member 202 is configured to have a shape that can suitably cover the mouth and nose of the user, and the threads 204 and 206 are provided for supporting or tying the cover member 202 to a head of the user. In an embodiment, the cover member 202 and threads 204, 206 may be made of a same material consisting of at least one of a cloth material or rubber, plastic or any combination thereof.

The respirator mask 200 also includes a filter 210 configured to prevent inhalation of pollutants by the user, an exhalation valve 212, a sensor configured (not shown, explained in conjunction with FIG. 3A-B) to determine the state of the exhalation valve 212, and a microprocessor 214 operatively coupled with the sensor. The microprocessor 214 includes Wi-Fi connectivity with a user mobile device (such as the wireless communication interface 130 of FIG. 1) for transmitting the sensed states of the exhalation valve 212 to a respirator mask manager (such as the respirator mask manager 114) of the user mobile device. The respirator mask 200 also includes batteries 216 for providing electrical power to the microprocessor 214 and the sensor. As shown, the respirator mask 200 includes a housing 220 for accommodating the above mentioned elements, such as the filter 210, the exhalation valve 212, the microprocessor 214, the batteries 216 and the sensor, of the respirator mask 200 therein. The housing 220 includes a plurality of opening 222 through which air can pass. The exhalation valve 212 is arranged (or positioned) behind the opening 222 and followed by the filter 210 for regulating the flow of the air (i.e. the exhalation valve 212 is configured to open and let exhaled air move out of the respirator mask 200 freely without having to go through the filter 210, and close when the user is breathing in). In one embodiment, the housing 220 may be configured to have a dimension of about 50 mm (millimetres)×45 mm.

Figure 3A:
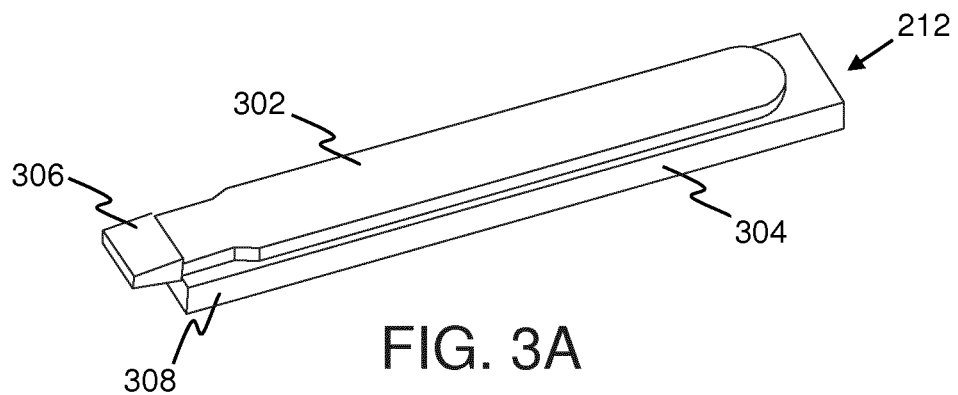
FIGS. 3A-B are schematic illustrations of an exhalation valve of the respirator mask, in accordance with an embodiment of the present disclosure.
Figure 3B:
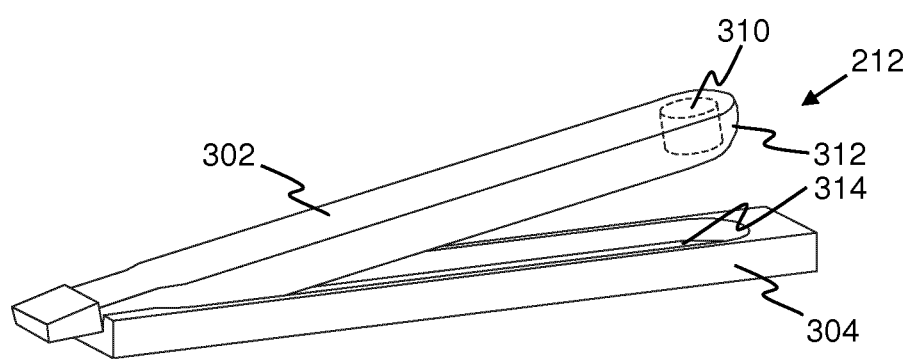

Referring now to FIG. 3A-B, illustrated are schematic illustrations of the exhalation valve 212, in accordance with an embodiment of the present disclosure. Specifically, FIGS. 3A-B schematically illustrate the exhalation valve 212 in a closed state and an open state (i.e. inactive and active states), respectively. As shown, the exhalation valve 212 is configured to have a flat elongated structure constituted by a first part 302 movable in nature and a second part 304 non-movable (or fixed) in nature. According to an embodiment, the first part 302 is hingedly coupled to the second part 304, particularly, an end portion 306 of the first part 302 is hingedly coupled to an end portion 308 of the second part 304. Therefore, the first part 302 is configured to hingedly coupled about the end portion 306 thereof with respect to the second part 304 with the flow of the air.

As shown in FIG. 3B, the first part 302 includes a magnet 310 (of the sensor arrangement, as mentioned above) arranged on an end portion 312 (opposite to the end portion 306) of the first part 302. The magnet 310 is configured to be operatively engaged with a hall sensor (not shown) of the sensor arrangement for determining states (closed state and an open state) of the exhalation valve 212. In one embodiment, the hall sensor may be arranged on the second part 304 of the exhalation valve 212, otherwise the hall sensor may be arranged on a suitable portion of the housing 220 (shown in FIG. 2), and operatively connected to the microprocessor 214 for sensing movement of the first part 302 with respect to the second part 304 (i.e. sensing opening and closing of the exhalation valve 212).

Figure 4:
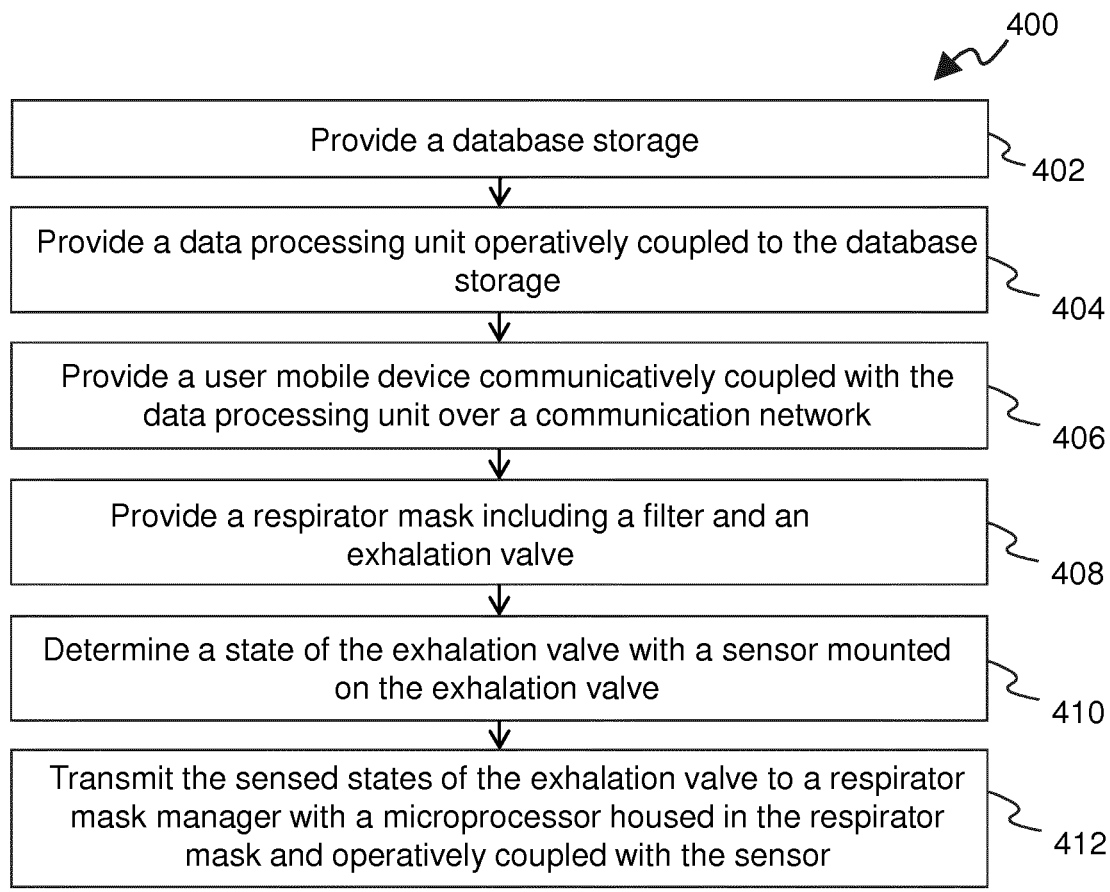
FIG. 4 is an illustration of steps of a method for respirator mask management, in accordance with an embodiment of the present disclosure.

Referring now to FIG. 4, illustrated are steps of a method 400 for respirator mask management, in accordance with an embodiment of the present disclosure. Specifically, those skilled in the art would recognize that the method 400 illustrates steps involved in implementing the system 100, explained in conjunction with the FIGS. 1-3.

At step 402, a database storage is provided.

At step 404, a data processing unit, is provided, which is operatively coupled to the database storage.

At step 406, a user mobile device, is provided, which is communicatively coupled with the data processing unit over a communication network. The user mobile device includes a respirator mask manager.

At step 408, a respirator mask, including a filter configured to prevent inhalation of pollutants by a user and an exhalation valve is provided.

At step 410, a state of the exhalation valve is determined with a sensor mounted on the exhalation valve.

At step 412, the sensed states of the exhalation valve is transmitted to the respirator mask manager with a microprocessor housed in the respirator mask and operatively coupled with the sensor. The microprocessor is configured to have a wireless connectivity with the user mobile device.

The steps 402 to 412 are only illustrative and other alternatives can also be provided where one or more steps are added, one or more steps are removed, or one or more steps are provided in a different sequence without departing from the scope of the claims herein. For example, the method 400 further includes (with the respirator mask manager) determining from the sensed and transmitted states of the exhalation valve whether a number of state changes experienced by the exhalation valve exceeds a pre-established threshold, and presenting a message to a display of the user mobile device indicating the filter is in need of replacement. Furthermore, the method 400 includes (with the respirator mask manager) presenting a button to the display of the user mobile device the actuation of which by the user presents an online order form for a replacement filter. Moreover, the method 400 includes (with the respirator mask manager), caching the sensed states of the exhalation valve on the user mobile device and relaying the sensed states to the database storage through the data processing unit. Additionally, the method 400 includes (with the respirator mask manager) receiving from the data processing unit, accumulated data regarding previously stored sensed states of the exhalation valve and presenting the accumulated data to the display of the user device. Also, in the method 400 the accumulated data regarding the previously stored sensed states of the exhalation valve includes times of day during which the respirator mask was worn, pollution levels at the time the respirator mask was worn, and an amount of time, a number of breaths, or a number of state changes remaining before the filter will need replacement. Further, the method 400 includes (with the microprocessor) scanning for one or more wireless access points to the communication network and when a scan discovers at least one wireless access point, collecting a wireless access point identifier of the discovered at least one wireless access point. Furthermore, the method 400 includes (with the respirator mask manager) deriving an approximate position of the respirator mask from the wireless access point identifier.

Figure 5:
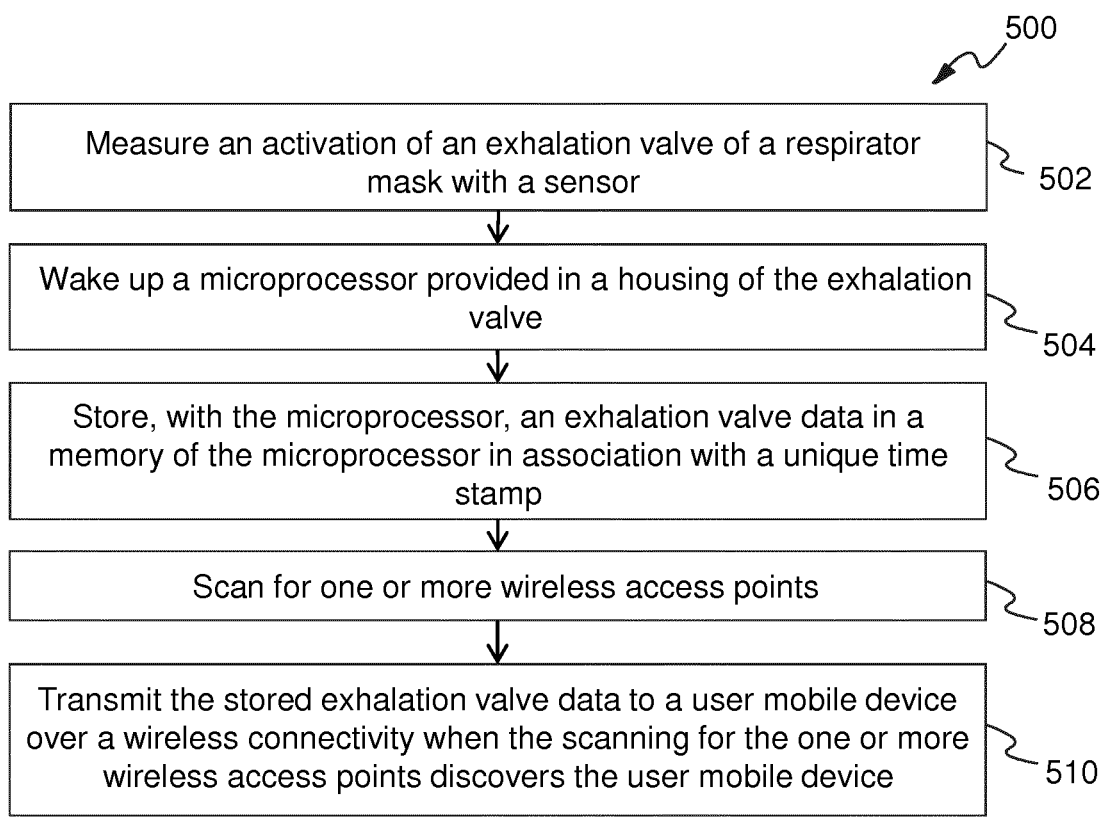
FIG. 5 is an illustration of steps of a method for managing the respirator mask, in accordance with an embodiment of the present disclosure.

Referring now to FIG. 5, illustrated are steps of a method 500 for managing a respirator mask, in accordance with an embodiment of the present disclosure. Specifically, those skilled in the art would recognize that the method 500 illustrates steps involved in using the respirator mask (such as the respirator mask 120 and 200), explained in conjunction with the FIGS. 1-3), explained in conjunction with the FIGS. 1-3.

At step 502, an activation of an exhalation valve of the respirator mask is measured with a sensor.

At step 504, a microprocessor, provided in a housing of the exhalation valve, is waken up.

At step 506, with the microprocessor, an exhalation valve data is stored in a memory of the microprocessor in association with a unique time stamp. Each of the exhalation valve activation is measured by the sensor.

At step 508, scan for wireless access points with a communication module of the microprocessor.

At step 510, the stored exhalation valve data is transmitted to a user mobile device over a wireless connectivity, when scanning for the wireless access discovers the user mobile device.

The steps 502 to 510 are only illustrative and other alternatives can also be provided where one or more steps are added, one or more steps are removed, or one or more steps are provided in a different sequence without departing from the scope of the claims herein. For example, the method 500 further comprises illuminating a light-emitting diode of the microprocessor, when the number of stored exhalation valve activations exceeds a pre-established threshold. Furthermore, the method 500 comprises transmitting the stored exhalation valve data to a data processing unit over a wireless connectivity without transmitting to the user mobile device, when the scanning for the one or more wireless access points discovers a wireless access point of a communication network. Additionally, the method 500 comprises waking up the microprocessor upon expiration of a time interval measured from the last measured exhalation valve activation; repeating the scanning and transmitting with the microprocessor; and checking the microprocessor, the sensor or both for errors, with the help of microprocessor.

The present disclosure provides a respirator mask, a respirator mask management system and methods for managing the respirator mask and the respirator mask management system. Specifically, the present disclosure enables in managing various aspects associated with a use of the respirator mask. For example, the present disclosure provides an efficient way to identify when a filter of the respirator mask should be changed. The identification for the change of the filter is made based on the different level of air pollution subject to the respirator mask. Additionally, the other aspects, associated with the use of the respirator mask, such as time and duration of wearing such respirator mask are also taken into consideration for identifying when the filter should be changed.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A respirator mask management system, comprising:
a data storage;
a data processing unit operatively coupled to the database storage;
a user mobile device communicatively coupled with the data processing unit over a communication network, the user mobile device including a respirator mask manager; and
a respirator mask including a filter configured to prevent inhalation of pollutants by a user, an exhalation valve, a sensor configured to determine a state of the exhalation valve, and a microprocessor operatively coupled with the sensor and having a wireless connectivity to the user mobile device for transmitting sensed states of the exhalation valve to the respirator mask manager;
wherein the respirator mask manager is configured to receive, from the microprocessor, the sensed states of the exhalation valve, determine whether a number of state changes experienced by the exhalation valve over a time interval exceeds a pre-established threshold, and present a message to a display of the user mobile device indicating the filter is in need of replacement when the number of changed states experienced by the exhalation valve over the time interval exceeds the pre-established threshold.

2. The system as set forth in claim 1, wherein the respirator mask manager is further configured to present a button to the display of the user mobile device, wherein an actuation of the button by the user, presents an online order form for a replacement filter.

3. The system as set forth in claim 1, wherein the respirator mask manager is further configured to:
cache, on the user mobile device, the sensed states of the exhalation valve transmitted by the microprocessor; and
relay the sensed states to the database storage through the data processing unit.

4. The system as set forth in claim 1, wherein the respirator mask manager is further configured to:
receive, from the data processing unit, accumulated data regarding previously stored sensed states of the exhalation valve; and
present the accumulated data to the display of the user mobile device.

5. The system as set forth in claim 4, wherein the accumulated data regarding the previously stored sensed states of the exhalation valve include times of day during which the respirator mask was used; pollution levels at the time the respirator mask was used; and an amount of time, a number of breaths, or a number of state changes remaining before the filter will need replacement.

6. The system as set forth in claim 1, wherein the microprocessor is programmed to scan for one or more wireless access points to the communication network and when a scan discovers at least one wireless access point, to collect a wireless access point identifier.

7. The system as set forth in claim 1, wherein the respirator mask manager is configured to derive an approximate position of the respirator mask from the wireless access point identifier.

8. A method for respirator mask management, comprising:
providing a database providing a data processing unit operatively coupled to the database storage; providing a user mobile device communicatively coupled with the data processing unit over a communication network and including a respirator mask manager; and providing a respirator mask including a filter configured to prevent inhalation of pollutants by a user and an exhalation valve; with a sensor mounted on the exhalation valve, determining a state of the exhalation valve; and with a microprocessor housed in the respirator mask and operatively coupled with the sensor, transmitting the sensed states of the exhalation valve to the respirator mask manager;
with the respirator mask manager, determining from the sensed and transmitted states of the exhalation valve whether a number of state changes experienced by the exhalation valve exceeds a pre-established threshold, and presenting a message to a display of the user mobile device indicating the filter is in need of replacement.

9. The method as set forth in claim 8, further comprising, with the respirator mask manager presenting a button to the display of the user mobile device, wherein an actuation of the button by the user, presents an online order form for a replacement filter.

10. The method as set forth in claim 8, further comprising, with the respirator mask manager caching the sensed states of the exhalation valve on the user mobile device and relaying the sensed states to the database storage through the data processing unit.

11. The method as set forth in claim 8, further comprising, with the respirator mask manager receiving, from the data processing unit, accumulated data regarding previously stored sensed states of the exhalation valve and presenting the accumulated data to the display of the user mobile device.

12. The method as set forth in claim 11, wherein the accumulated data regarding the previously stored sensed states of the exhalation valve include times of day during which the respirator mask was worn; pollution levels at the time the respirator mask was worn; and an amount of time, a number of breaths, or a number of state changes remaining before the filter will need replacement.

13. The method as set forth in claim 8, further comprising, with the microprocessor, scanning for one or more wireless access points to the communication network and when a scan discovers at least one wireless access point, collecting a wireless access point identifier of the at least one discovered wireless access point.

14. The method as set forth in claim 13, further comprising, with the respirator mask manager, deriving an approximate position of the respirator mask from the wireless access point identifier.

* * * * *